(12) United States Patent
Smejkal et al.

(10) Patent No.: US 9,815,829 B2
(45) Date of Patent: Nov. 14, 2017

(54) PROCESS FOR THE PREPARATION OF OPTICALLY ACTIVE ISOXAZOLINE COMPOUNDS

(71) Applicant: Syngenta Participations AG, Basel (CH)

(72) Inventors: Tomas Smejkal, Stein (CH); Helmars Smits, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/501,008

(22) PCT Filed: Aug. 4, 2015

(86) PCT No.: PCT/EP2015/067894
§ 371 (c)(1),
(2) Date: Feb. 1, 2017

(87) PCT Pub. No.: WO2016/023787
PCT Pub. Date: Feb. 18, 2016

(65) Prior Publication Data
US 2017/0217953 A1    Aug. 3, 2017

(30) Foreign Application Priority Data

Aug. 11, 2014 (EP) .................... 14180467
Apr. 23, 2015 (EP) .................... 15164843

(51) Int. Cl.
*C07D 215/00* (2006.01)
*C07D 261/14* (2006.01)
(Continued)

(52) U.S. Cl.
CPC ........ *C07D 453/04* (2013.01); *B01J 31/0244* (2013.01); *C07D 261/14* (2013.01)

(58) Field of Classification Search
CPC .................................................. C07D 215/00
(Continued)

(56) References Cited

U.S. PATENT DOCUMENTS 6,596,870 B2 *    7/2003    Pochapsky ........... B01J 31/0239
546/126

FOREIGN PATENT DOCUMENTS

WO        0205953 A3       1/2002
WO        2011067272 A1    6/2011
(Continued)

OTHER PUBLICATIONS

Tari, Silvia et al: "Enantioselective Michael reaction of B-Keto esters organocatalyzed by recoverable Cincona-derived dimeric ammonium salts" in: Tetrahedron Asymmetry (20/23), Dec. 11, 2009, pp. 2651-2654. XP26835996A.
(Continued)

*Primary Examiner* — Niloofar Rahmani
(74) *Attorney, Agent, or Firm* — R. Kody Jones

(57) ABSTRACT

The present invention relates to a process for the preparation of a compound of formula (I) wherein $A_1$ and $A_2$ are C—H, or one of $A_1$ and $A_2$ is C—H and the other is N; $R_1$ is $C_1$-$C_4$alkyl, $C_1$-$C_4$haloalkyl or $C_3$-$C_6$cycloalkyl; each $R_2$ is independently bromo, chloro, fluoro or trifluoromethyl; $R_3$ is hydrogen; $R_4$ is hydrogen, halogen, methyl, halomethyl or cyano; or $R_3$ and $R_4$ together form a bridging 1,3-butadiene group; $R_5$ is chlorodifluoromethyl or trifluoromethyl; n is 2 or 3; by reacting a compound of formula (II) wherein $A_1$, $A_2$, $R_1$, $R_2$, $R_3$, $R_4$, $R_5$ and n is as defined under formula (I) above, with hydroxylamine, a base and a chiral catalyst, characterized in that the chiral catalyst is a dimeric chiral catalyst of formula (III) wherein $R_6$, $R_7$, $R_8$, $R_9$, $R_{10}$ and X are as defined in claim 1.

9 Claims, No Drawings

(51) Int. Cl.
*C07D 453/04* (2006.01)
*B01J 31/02* (2006.01)

(58) Field of Classification Search
USPC .......................................... 546/152
See application file for complete search history.

(56) References Cited

FOREIGN PATENT DOCUMENTS

| WO | 2011104089 A1 | 9/2011 |
| WO | 2011161130 A1 | 12/2011 |
| WO | 2013069731 A1 | 5/2013 |

OTHER PUBLICATIONS

Kazutaka Matoba et al: "Enantioselective Synthesis of Trifluoromethyl-substituted 2-isocazolines: Asymmetric Hydroxylamine/Enone Cascade Reaction" in: Angewandte Chemie international edition (49/33), Aug. 2, 2010, pp. 5762-5766. XP 55003070A.
International Search Report and Written Opinion for PCT/EP2015/067894, dated Sep. 24, 2015.
Extended European Search Report for EP14180467.4, dated Nov. 12, 2014.

* cited by examiner

PROCESS FOR THE PREPARATION OF OPTICALLY ACTIVE ISOXAZOLINE COMPOUNDS

RELATED APPLICATION INFORMATION

This application is a 371 of International Application No. PCT/EP2015/067894, filed 4 Aug. 2015, which claims priority to EP 14180467.4, filed 11 Aug. 2014, and EP 15164843.3, filed 23 Apr. 2015, the contents of which are incorporated herein by reference herein.

The present invention relates to a process for the preparation of optically active isoxazoline compounds with cycloserine substituent which are useful as pesticides and to catalysts for the use in said process.

Processes for the preparation of optically active isoxazoline compounds using chiral catalysts are described, for example, in WO 2013/069731. Optically active isoxazoline compounds with cycloserine substituent show two stereocentres which configuration is important for the biological activity of the compounds. The monomeric catalysts according to WO 2013/069731 are based on cinchona alkaloids and show high enantioselectivity for the isoxazoline formation. However, significant racemisation of the cycloserine stereocenter can be observed which reduces the selectivity of the reaction and therefore the yield of the desired optically active product. This is a significant disadvantage in particular for large scale production.

It is therefore the object of the present invention to provide a process for the preparation of optically active isoxazoline compounds with cycloserine substituent which process improves the enantioselectivity of the desired product by the use of an innovative catalyst.

Thus, according to the present invention, there is provided a process for the preparation of a compound of formula I

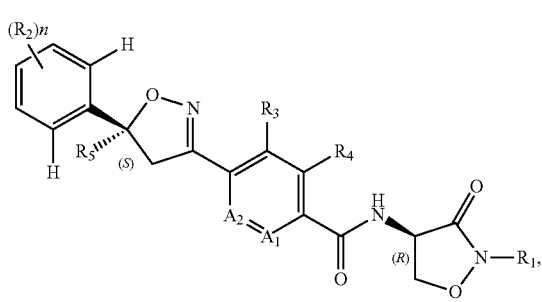

wherein $A_1$ and $A_2$ are C—H, or one of $A_1$ and $A_2$ is C—H and the other is N;

$R_1$ is $C_1$-$C_4$alkyl, $C_1$-$C_4$haloalkyl or $C_3$-$C_6$cycloalkyl;

each $R_2$ is independently bromo, chloro, fluoro or trifluoromethyl;

$R_3$ is hydrogen;

$R_4$ is hydrogen, halogen, methyl, halomethyl or cyano;

or $R_3$ and $R_4$ together form a bridging 1,3-butadiene group;

$R_5$ is chlorodifluoromethyl or trifluoromethyl;

n is 2 or 3;

by reacting a compound of formula II

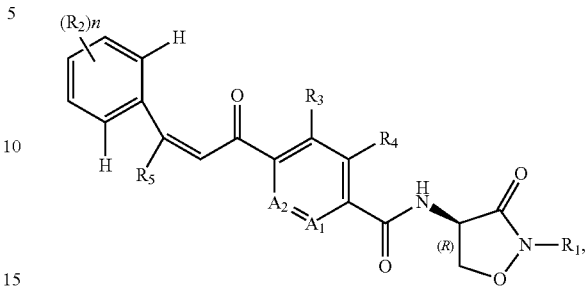

wherein $A_1$, $A_2$, $R_1$, $R_2$, $R_3$, $R_4$, $R_5$ and n is as defined under formula I above, with hydroxylamine, a base and a chiral catalyst, characterized in that the chiral catalyst is a dimeric chiral catalyst of formula III

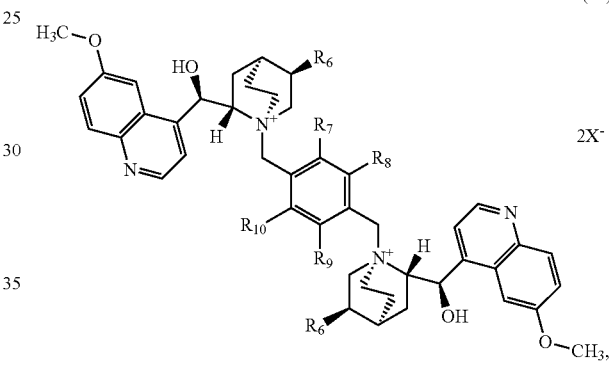

wherein each $R_6$ is ethyl or vinyl;

$R_7$, $R_8$, $R_9$ and $R_{10}$ are halogen, cyano, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfonyl or $C_1$-$C_6$haloalkylsulfonyl; and X is a halogen anion, $BF_4^-$, $PF_6^-$, $HSO_4^-$ or an $C_1$-$C_3$alkylsulfonate, benzenesulfonate or methyl-benzenesulfonate.

The alkyl groups occurring in the definitions of the substituents can be straight-chain or branched and are, for example, methyl, ethyl, n-propyl, n-butyl, n-pentyl, n-hexyl, iso-propyl, n-butyl, sec-butyl, iso-butyl or tert-butyl. Alkoxy, haloalkyl, haloalkoxy, alkylsulfonyl and haloalkylsulfonyl radicals are derived from the alkyl radicals mentioned.

Halogen is generally fluorine, chlorine, bromine or iodine, preferably fluorine, bromine or chlorine. This also applies, correspondingly, to halogen in combination with other meanings, such as haloalkyl or haloalkoxy.

Haloalkyl groups preferably have a chain length of from 1 to 4 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Alkoxy is, for example, methoxy, ethoxy, propoxy, i-propoxy, n-butoxy, isobutoxy, sec-butoxy and tert-butoxy; preferably methoxy and ethoxy. Halogenalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy. Alkylthio is, for example, methylthio, ethylthio, propylthio, isopropylthio, n-butylthio, isobutylthio, sec-butylthio or tert-butylthio, preferably methylthio and ethylthio.

In the process of the invention, compounds of formula III are preferred, wherein X is a halogen anion, $BF_4^-$ or $HSO_4^-$.

Preferred $C_1$-$C_3$alkylsulfonates and methyl-benzenesulfonates are methanesulfonate, ethanesulfonate, propanesulfonate, benzenesulfonate and 4-methyl-benzenesulfonate.

If n is 2, the compounds of formula I are preferably represented by the compounds of formula Ia

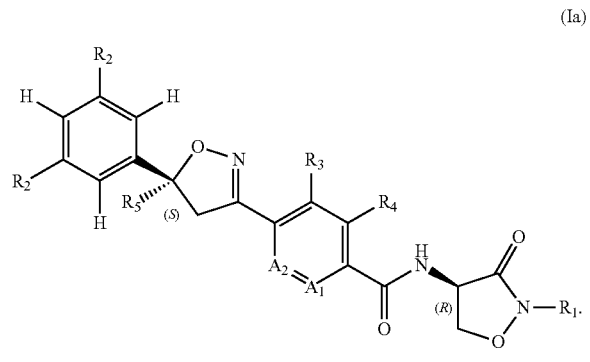

(Ia)

The process according to the invention is especially suitable for the preparation of compounds of formula I, wherein $A_1$ and $A_2$ are C—H;
$R_1$ is $C_1$-$C_4$alkyl;
each $R_2$ is independently chloro, fluoro or trifluoromethyl; preferably chloro or fluoro;
$R_3$ is hydrogen;
$R_4$ is hydrogen, halogen, methyl, halomethyl or cyano; preferably methyl;
$R_5$ is trifluoromethyl; and
n is 2 or 3.

The dimeric chiral catalyst of formula III

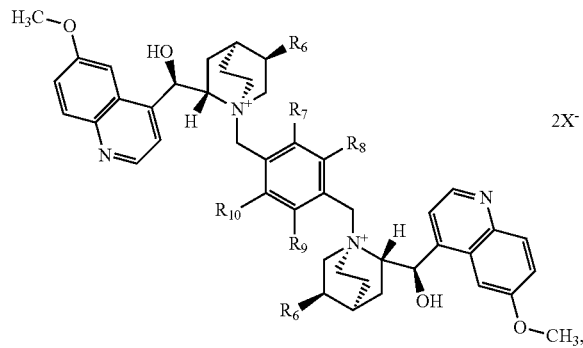

(III)

wherein each $R_6$ is ethyl or vinyl;
$R_7$, $R_8$, $R_9$ and $R_{10}$ are halogen, cyano, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfonyl or $C_1$-$C_6$haloalkylsulfonyl; and
X is a halogen anion, $BF_4^-$ or $PF_6^-$; is novel and was especially developed for the process according to this invention. The dimeric chiral catalyst of formula III therefore represents a further object of the invention.

Preferred catalysts of formula III are those, wherein
each $R_6$ is vinyl;
each of the substituents $R_7$, $R_8$, $R_9$ and $R_{10}$ has the same meaning and represent halogen and X is chloride, bromide or $BF_4^-$, in particular chloride or bromide.

Especially preferred catalysts of formula III are those, wherein
each $R_6$ is vinyl;
each of the substituents $R_7$, $R_8$, $R_9$ and $R_{10}$ has the same meaning and represent fluoro or chloro, especially fluoro; and X is chloride or bromide.

The catalysts of formula III can be prepared by reacting a compound of formula IV

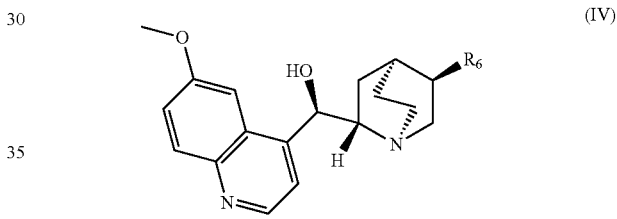

(IV)

wherein
$R_6$ is ethyl or vinyl;
with a compound of formula V

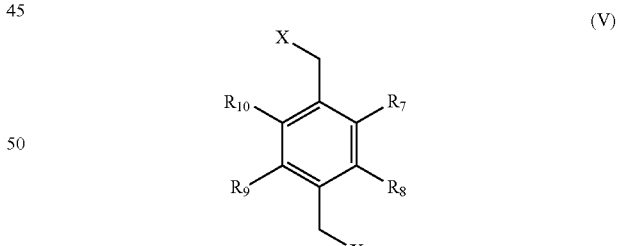

(V)

wherein $R_6$, $R_7$, $R_8$, $R_9$, $R_{10}$ and X are as defined for the compound of formula III above. The process is preferably performed in an organic solvent, e.g. toluene or acetonitrile or methanol. Preparation methods for monomeric chiral catalysts are described, for example, in WO 2013/069731. Said methods can be used analogously to prepare the catalysts of formula III according to the invention. Compounds of formula IV are known and commercially available or may be prepared according to known methods.

The compounds of formula V can be prepared for example by reacting a compound of formula (VI)

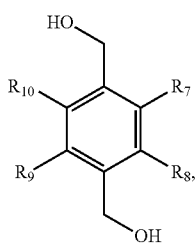

(VI)

with a suitable halogenating reagents such as SOCl$_2$, POCl$_3$, SOBr$_2$, POBr$_3$, PBr$_3$, PCl$_3$, HBr or HCl.

Further, the compounds of formula V can be prepared for example by reacting a compound of formula (VII)

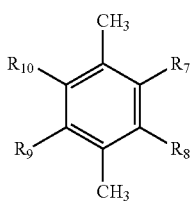

(VII)

wherein R$_7$, R$_8$, R$_9$ and R$_{10}$ are as defined under formula V above, with a suitable halogenating reagents such as Cl$_2$, Br$_2$, NCS or NBS.

Further, the compounds of formula V can be prepared by for example by reacting a compound of formula (VIII)

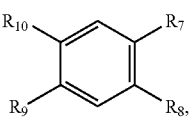

(VIII)

wherein R$_7$, R$_8$, R$_9$ and R$_{10}$ are as defined under formula V above, with a suitable halomethylating reagent such as CH$_2$O/HCl, CH$_2$O/HCl/ZnCl$_2$, CH$_2$O/HBr.

The compounds of formula II can be prepared, for example according to WO 2011/067272, in particular shown in Scheme 3 on page 18-19.

The process according to the invention is preferably carried out in a suitable organic solvent, for example dichloromethane, 1,2-dichloroethane, toluene, chlorobenzene, chloroform, tert-butyl methyl ether, iso-propanol, ethanol, tetrahydrofurane, 2-methyltetrahydrofurane, acetonitrile, propionitrile, 2-methylpropionitrile, butyronitrile preferably 1,2-dichloroethane, 2-methyltetrahydrofurane, acetonitrile or dichloromethane at a temperature of between −78° C. to 60° C., preferably between −20° C. and +20° C., and at a dilution of e.g. between 0.1 M to 1 M. The reaction time is usually between 30 minutes and 48 hours, preferably between 1 and 4 hours. The amount of catalyst is usually from 0.01 to 0.4 molar equivalents, preferably from 0.02 to 0.2 molar equivalents. The amount of hydroxylamine is from 1 to 10 equivalents, preferably from 1.0 to 1.2 equivalents. Such reactions are usually carried out in the presence of a base. Suitable bases include alkali hydroxides such as lithium hydroxide, sodium hydroxide or potassium hydroxide, preferably sodium hydroxide, in usual amounts of between 0.05 and 2 equivalents. Preferably the amount of base used is from 0.05 to 1.0 equivalents. The reaction may be carried out in the presence of water.

PREPARATORY EXAMPLES

The following abbreviations were used in this section: s=singlet; bs=broad singlet; d=doublet; dd=double doublet; dt=double triplet; t=triplet; tt=triple triplet, q=quartet, sept=septet; m=multiplet; Me=methyl; Et=ethyl; Pr=propyl; Bu=butyl; M.p.=melting point; RT=retention time, M=molecular mass.

The following LC-MS methods were used to characterize the compounds:

Method A

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 1.2-1.5 min 100% B; Flow (ml/min) 0.85.

Method B

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 2.7-3.0 min 100% B; Flow (ml/min) 0.85.

Chiral HPLC was conducted on a Waters UPLC—Hclass, DAD Detector Waters UPLC, with a column Daicel CHIRALPAK® ID, 5 µl, 0.46 cm×25 cm, Mobile phase: Hept/EtOAc 70/30, Flow rate: 1.0 ml/min, Detection: 265 nm, Sample concentration: 1 mg/mL in DCM/iPrOH 50/50, Injection: 2 µl. Free radicals represent methyl groups.

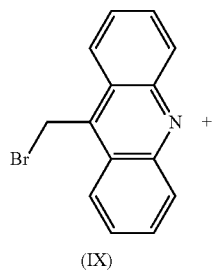

(IX)

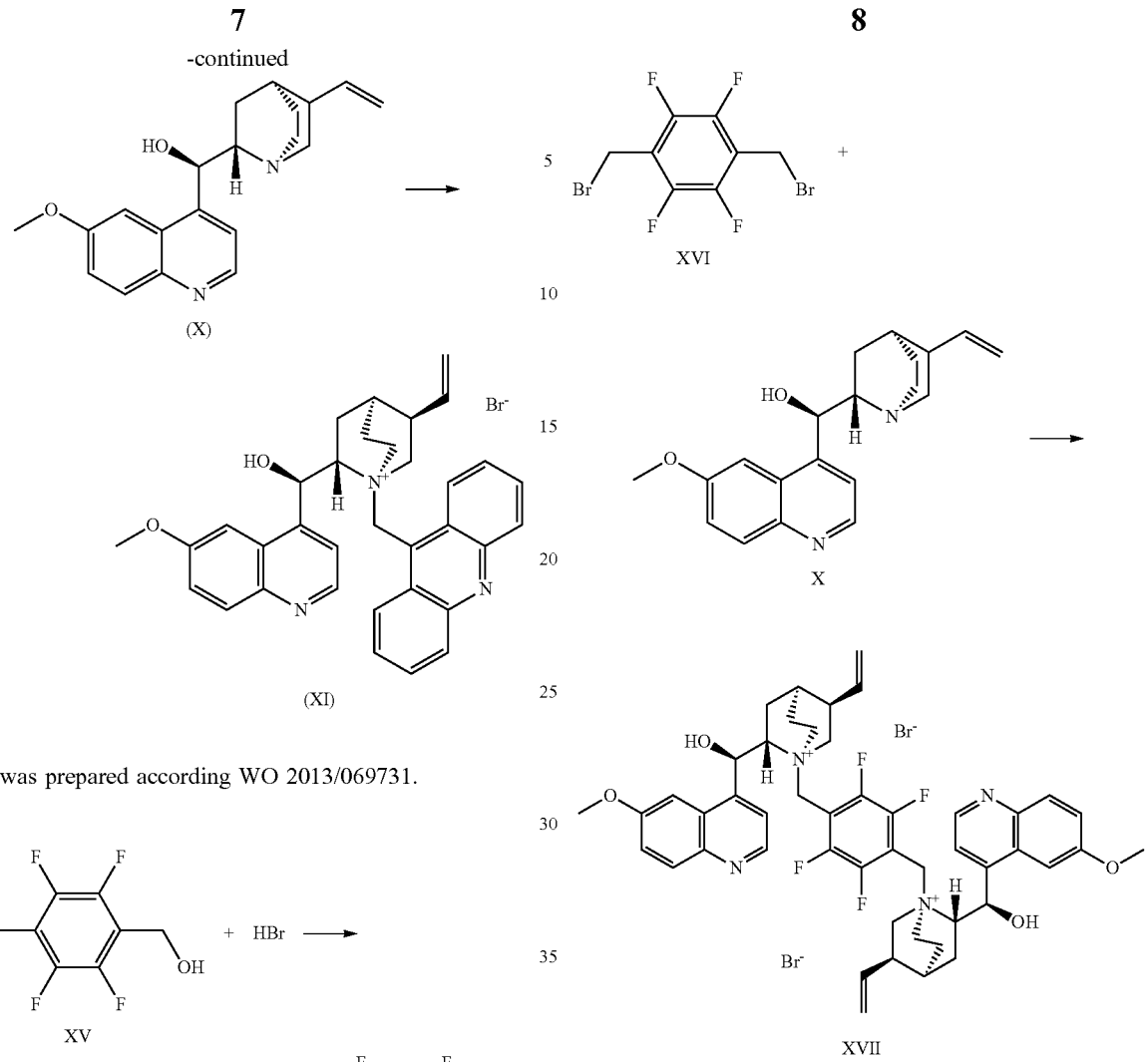

(XI) was prepared according WO 2013/069731.

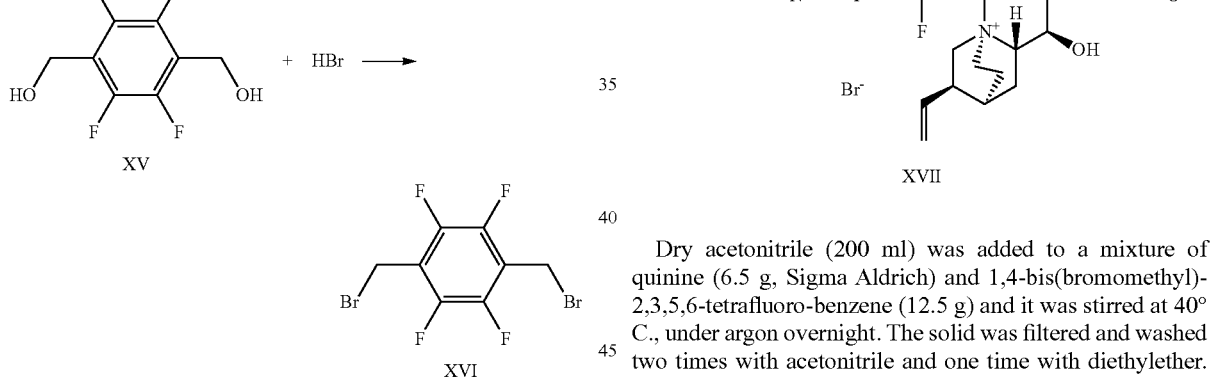

[2,3,5,6-tetrafluoro-4-(hydroxymethyl)phenyl] methanol XV (5.0 g) was mixed with HBr in acetic acid (5.7 mol/L, 41 ml). The resulting dark orange solution was stirred for 16 hours at ambient temperature.

10 mL of acetic acid was added and the stirring was continued for another 20 hours. Work up: The orange suspension was diluted with ethyl acetate- ->orange solution. This solution was transferred into an additional funnel and it was added dropwise to a cold saturated $Na_2CO_3$ solution (gas evolution). At the end of addition, the reaction mixture was stirred for another 20 minutes. Then the aqueous layer (suspension) was extracted twice with ethyl acetate. The organic layer was washed twice with saturated $Na_2CO_3$ solution and once with brine. Then it was dried over $Na_2SO_4$, filtered and evaporated to give 7.5 g of the product XVI as a yellowish solid.

$^1$H NMR (400 MHz, CDCl$_3$) δ=4.52 (s, 4H). $^{19}$F NMR (376 MHz, CDCl$_3$) δ=142.36.

Dry acetonitrile (200 ml) was added to a mixture of quinine (6.5 g, Sigma Aldrich) and 1,4-bis(bromomethyl)-2,3,5,6-tetrafluoro-benzene (12.5 g) and it was stirred at 40° C., under argon overnight. The solid was filtered and washed two times with acetonitrile and one time with diethylether. It was dried under reduced pressure to give 18.0 g of the product XVII as a beige solid.

$^1$H NMR (400 MHz, DMSO) δ=8.83 (d, 2H, J=4.4), 8.02 (d, 2H, J=8.3), 7.80-7.79 (m, 2H), 7.51 (d, 2H, J=4.9), 7.44 (br.s, 2H), 6.81 (br.s, 2H), 6.58 (br.s, 2H), 5.82-5.76 (m, 2H), 5.62 (d, 2H, J=12.8), 5.13-5.03 (m, 4H), 4.83 (d, 2H, J=12.8), 4.20 (br.s, 6H), 4.03 (s, 6H), 3.86 (br.s, 26H), 3.68 (br.s, 2H), 2.87 (br.s, 2H), 2.24 (br.s, 2H), 2.17 (br.s, 2H), 2.05 (d, 2H), 1.89 (br.s, 2H), 1.44 (t, 2H).

LC-MS (ES+): m/z=413 (M-569) RT=0.76 (Method A)

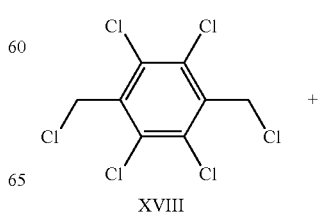

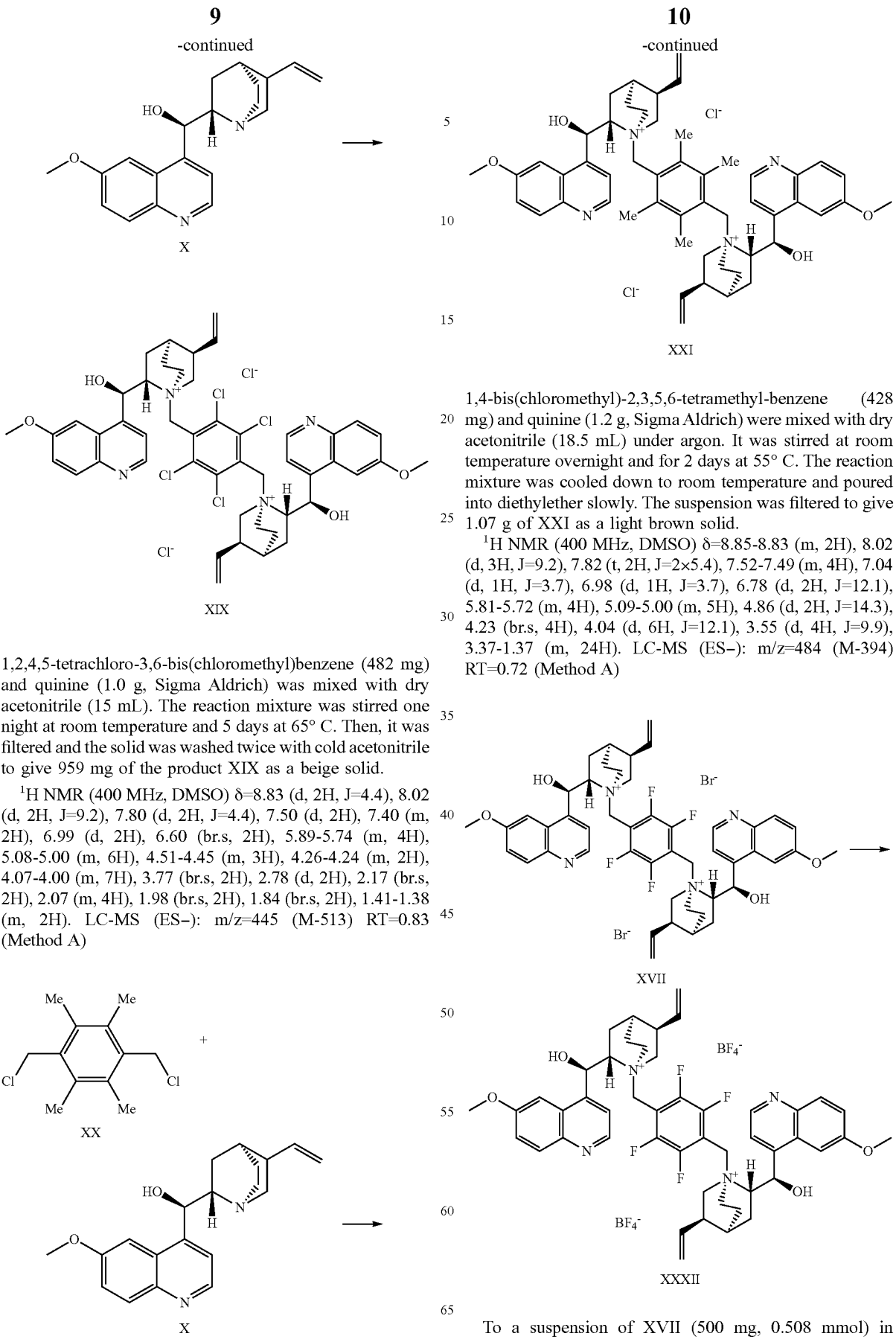

1,2,4,5-tetrachloro-3,6-bis(chloromethyl)benzene (482 mg) and quinine (1.0 g, Sigma Aldrich) was mixed with dry acetonitrile (15 mL). The reaction mixture was stirred one night at room temperature and 5 days at 65° C. Then, it was filtered and the solid was washed twice with cold acetonitrile to give 959 mg of the product XIX as a beige solid.

$^1$H NMR (400 MHz, DMSO) δ=8.83 (d, 2H, J=4.4), 8.02 (d, 2H, J=9.2), 7.80 (d, 2H, J=4.4), 7.50 (d, 2H), 7.40 (m, 2H), 6.99 (d, 2H), 6.60 (br.s, 2H), 5.89-5.74 (m, 4H), 5.08-5.00 (m, 6H), 4.51-4.45 (m, 3H), 4.26-4.24 (m, 2H), 4.07-4.00 (m, 7H), 3.77 (br.s, 2H), 2.78 (d, 2H), 2.17 (br.s, 2H), 2.07 (m, 4H), 1.98 (br.s, 2H), 1.84 (br.s, 2H), 1.41-1.38 (m, 2H). LC-MS (ES−): m/z=445 (M-513) RT=0.83 (Method A)

1,4-bis(chloromethyl)-2,3,5,6-tetramethyl-benzene (428 mg) and quinine (1.2 g, Sigma Aldrich) were mixed with dry acetonitrile (18.5 mL) under argon. It was stirred at room temperature overnight and for 2 days at 55° C. The reaction mixture was cooled down to room temperature and poured into diethylether slowly. The suspension was filtered to give 1.07 g of XXI as a light brown solid.

$^1$H NMR (400 MHz, DMSO) δ=8.85-8.83 (m, 2H), 8.02 (d, 3H, J=9.2), 7.82 (t, 2H, J=2×5.4), 7.52-7.49 (m, 4H), 7.04 (d, 1H, J=3.7), 6.98 (d, 1H, J=3.7), 6.78 (d, 2H, J=12.1), 5.81-5.72 (m, 4H), 5.09-5.00 (m, 5H), 4.86 (d, 2H, J=14.3), 4.23 (br.s, 4H), 4.04 (d, 6H, J=12.1), 3.55 (d, 4H, J=9.9), 3.37-1.37 (m, 24H). LC-MS (ES−): m/z=484 (M-394) RT=0.72 (Method A)

To a suspension of XVII (500 mg, 0.508 mmol) in acetonitrile (4 ml) was added KBF$_4$ (0.320 g, 2.54 mmol).

The reaction mixture was stirred at room temperature for 2.5 days. Diethyl ether was added to the reaction mixture. The resulting precipitate was filtered off and washed with water. The precipitate was dissolved in a mixture of methanol and dichloromethane and evaporated under reduced pressure to afford XXXII (474 mg) as a beige solid.

IR (thin film) 1621, 1496, 1292, 1241, 1025 cm$^{-1}$

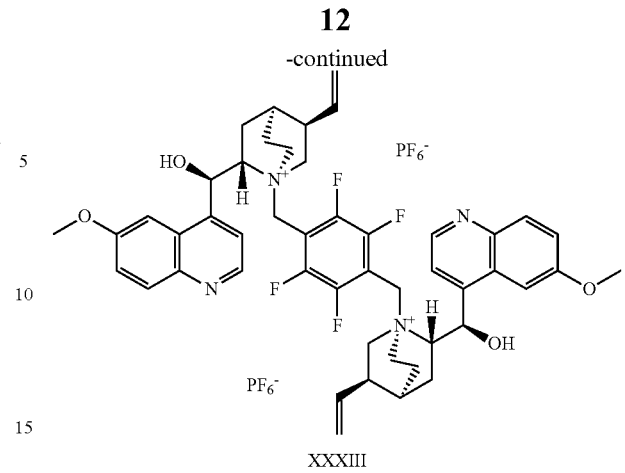

XXXIII

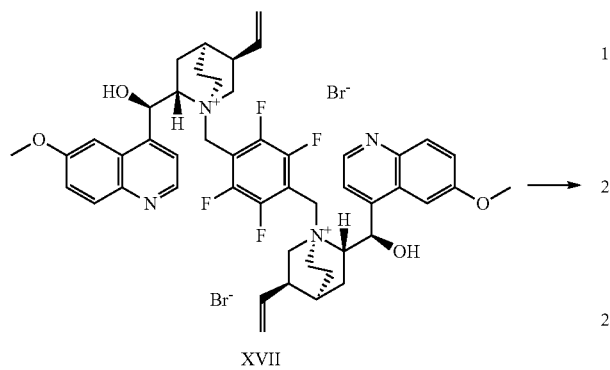

XVII

To a suspension of catalyst XVII (500 mg, 0.508 mmol) in acetonitrile (4 ml) was added KPF$_6$ (0.467 g, 2.54 mmol). The reaction mixture was stirred at room temperature for 2.5 days. Diethyl ether was added to the reaction mixture. The resulting precipitate was filtered off and washed with water. The precipitate was dissolved in a mixture of methanol and dichloromethane and evaporated under reduced pressure to afford XXXIII (433 mg) as a brown solid.

IR (thin film) 1621, 1497, 1293, 1241, 1026, 928, 826 cm$^{-1}$

The selectivity of the catalysts according to this invention was compared with structurally close catalysts according to the prior art. The results are given in Table 1 below (free radicals represent methyl groups):

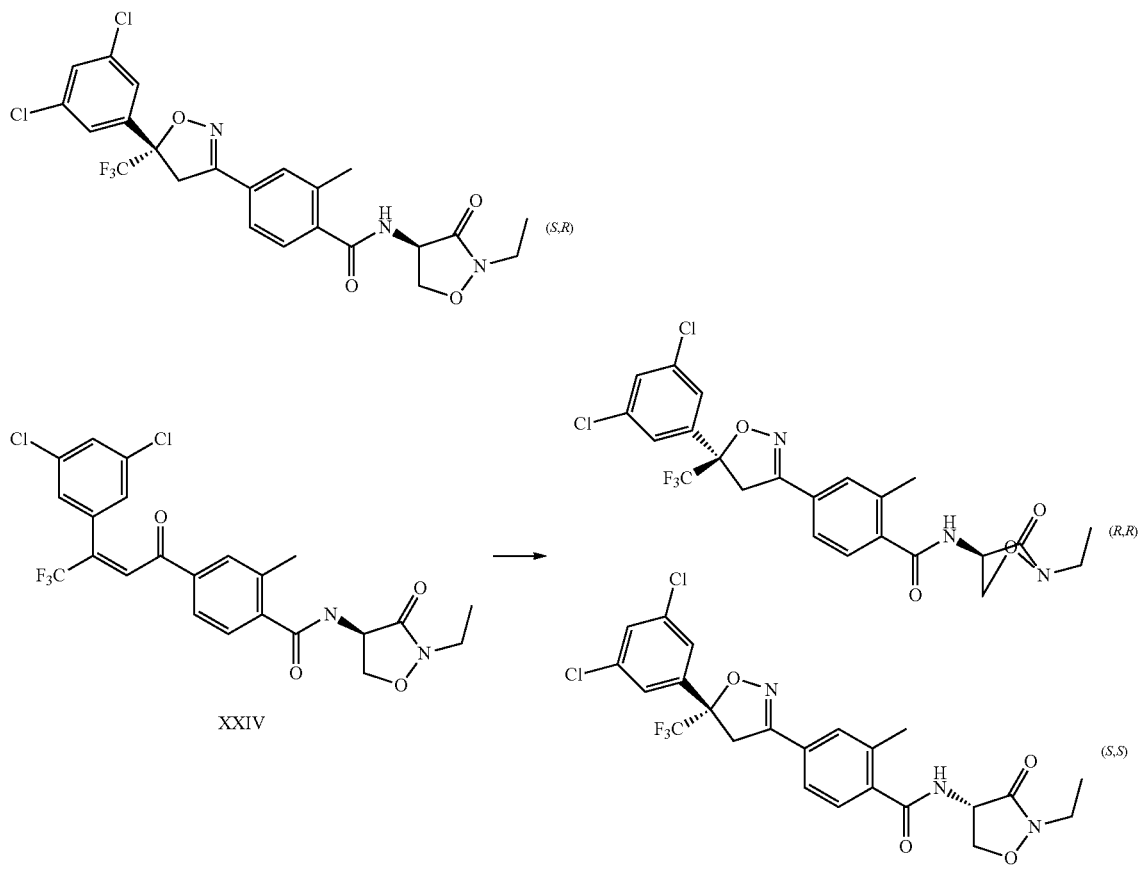

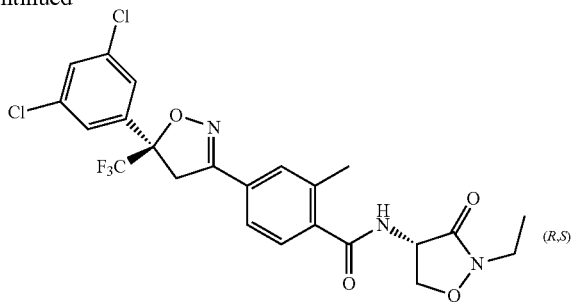

XXV

General procedure (based on WO 2013/069731):

0.32 mmol of XXIV (E/Z>99:1, R/S=99:1) was dissolved in 4 mL of dichloromethane. Catalyst 0.06 mmol or 0.03 mmol (as indicated below) was added. The reaction mixture was cooled down to −20° C., 0.7 mmol of 10M sodium hydroxide solution, 0.054 ml of water and 0.64 mmol of 50% aqueous hydroxylamine were sequentially added. The reaction mixture was vigorously stirred at −20° C. for 20 h and analysed by chiral HPLC (ratio of diastereomers) and 1H NMR (conversion).

TABLE 1 comparative data with catalysts known from the prior art:

| Catalyst | HPLC ratio of diastereomers (S,S:R;S:S,R:R,R) |
| --- | --- |
| Compound XI according to WO 2013/069731 0.06 mmol | 19:1:77:3 |
| Compound XXX according to WO 2011/104089 and WO 2011/067272 0.06 mmol | 10:2:72:16 |
| Compound XXXI according to WO 2002/05953 | 4:2:64:30 (*) |
| Compound XVII according to this invention 0.06 mmol | 3:0:94:3 |
| Compound XVII according to this invention 0.03 mmol | 4:1:92:3 |
| Compound XIX according to this invention 0.06 mmol | 5:1:90:4 |
| Compound XIX according to this invention 0.03 mmol | 5:1:90:4 |

(*) 86% conversion of the starting material. More than >95% conversion of the starting material was observed for all other runs.

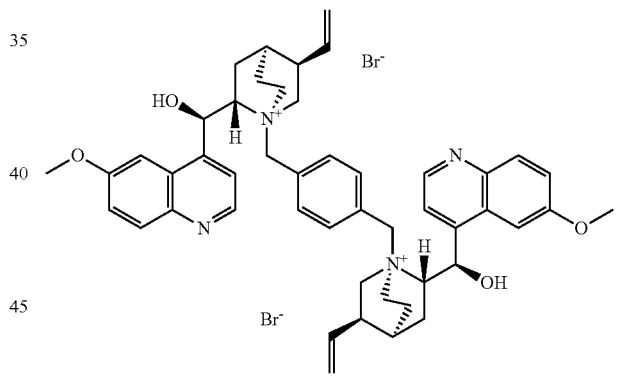

XXX according to WO 2011/104089 and WO 2011/0672726

XXXI according to WO 2002/05953

TABLE 2

Examples of catalysts according to the invention with different reaction conditions

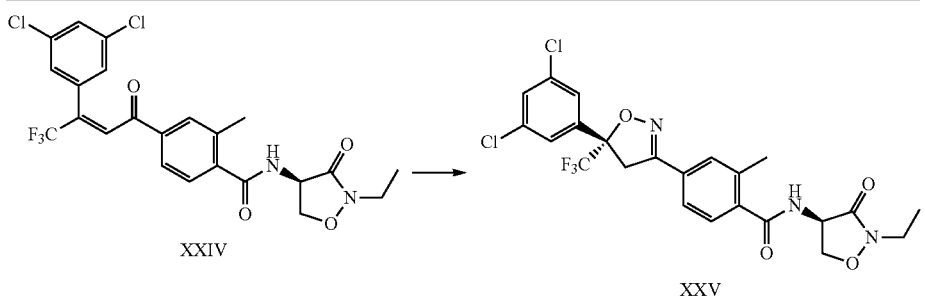

General procedure:

0.32 mmol of XXIV (E/Z>99:1, R/S=99:1) was dissolved in 4 mL of dichloromethane. Catalyst 0.06 mmol was added. The reaction mixture was cooled down to −20° C., 0.7 mmol of 10M sodium hydroxide solution, 0.054 ml of water and 0.64 mmol of 50% aqueous hydroxylamine were sequentially added. The reaction mixture was vigorously stirred at −20° C. for 20 h and analysed by chiral HPLC (ratio of diastereomers) and 1H NMR (conversion).

| Catalyst | HPLC ratio of diastereomers (S,S:R;S:S,R:R,R) |
| --- | --- |
| Compound XXI 0.06 mmol | 10:5:59:26 |

More than >95% conversion of the starting material was observed for all runs.

TABLE 3

Selectivity of catalysts according to this invention with different reaction conditions:

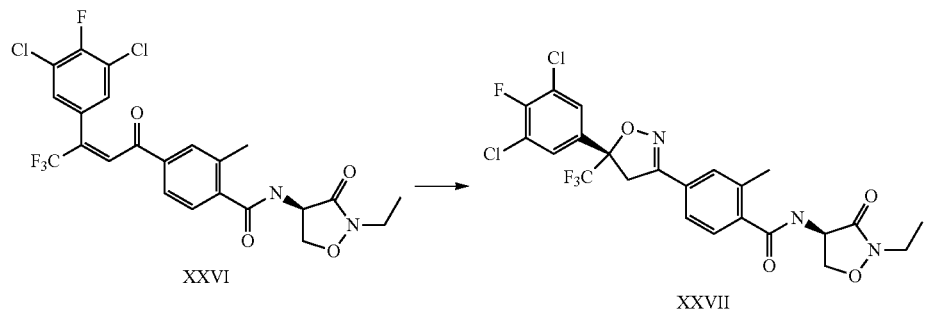

General procedure:

XXVI (E/Z>99:1, R/S>99:1) and catalyst XVII were stirred in the given solvent at the reaction temperature. Aqueous 5-10M solution of base and 50% aqueous hydroxylamine were added sequentially. The reaction mixture was vigorously stirred at the given temperature. It was analysed by chiral HPLC (ratio of diastereomers) and 1H NMR using 1,3,5-trimethoxybenzene as a standard (yield determination).

| Scale | Catalyst/catalysts loading [%] | Reaction conditions | Chemical Yield | HPLC ratio of diastereomers (S,S:R,S:S,R:R,R) |
| --- | --- | --- | --- | --- |
| 1 g | Compound XVII 0.025 eq | 1.1 eq NH2OH, 0.16 eq KOH, DCM solvent, −10° C., 1.5 h | 86% | 1:0:89:9 |
| 10 g | Compound XVII 0.05 eq | 1.1 eq NH$_2$OH, 0.16 eq NaOH, DCE solvent, RT, 20 min | 83% | 7:1:85:7 |
| 1 g | Compound XVII 0.10 eq | 2 eq NH$_2$OH, 0.1 eq KOH, iPrOH solvent, 0° C., 3 h | 60% | 0:0:93:7 |
| 1 g | Compound XXXII 0.05 eq | 1.1 eq NH$_2$OH, 0.16 eq NaOH, DCE solvent, −10° C., 4.5 h | 79% | 3:0:92:5 |

The invention claimed is:

1. A process for the preparation of a compound of formula I

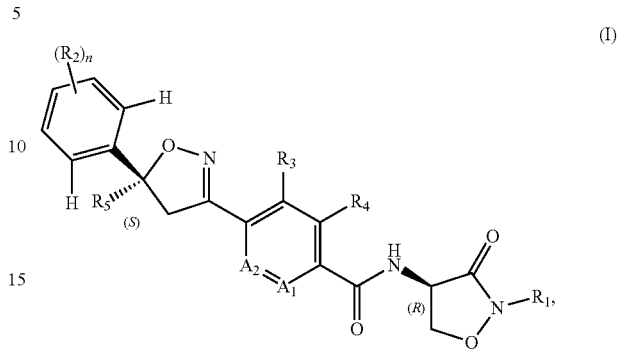

wherein $A_1$ and $A_2$ are C—H, or one of $A_1$ and $A_2$ is C—H and the other is N;

$R_1$ is $C_1$-$C_4$alkyl, $C_1$-$C_4$haloalkyl or $C_3$-$C_6$cycloalkyl;

each $R_2$ is independently bromo, chloro, fluoro or trifluoromethyl;

$R_3$ is hydrogen;

$R_4$ is hydrogen, halogen, methyl, halomethyl or cyano;

or $R_3$ and $R_4$ together form a bridging 1,3-butadiene group;
$R_5$ is chlorodifluoromethyl or trifluoromethyl;
n is 2 or 3;
by reacting a compound of formula II

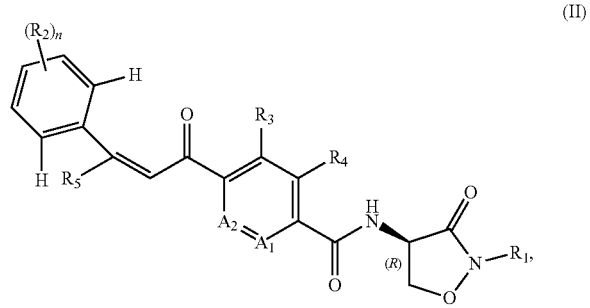

wherein
$A_1$, $A_2$, $R_1$, $R_2$, $R_3$, $R_4$, $R_5$ and n is as defined under formula I above, with hydroxylamine, a base and a chiral catalyst, characterized in that the chiral catalyst is a dimeric chiral catalyst of formula III

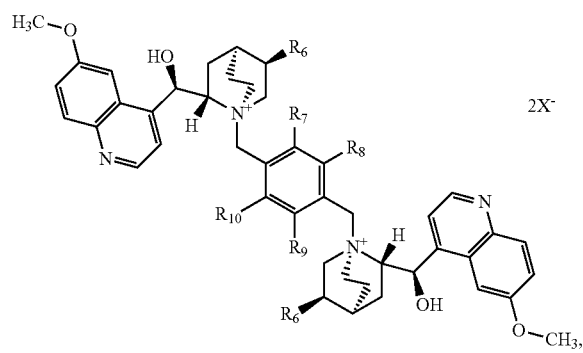

wherein
each $R_6$ is ethyl or vinyl;
$R_7$, $R_8$, $R_9$ and $R_{10}$ are halogen, cyano, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfonyl or $C_1$-$C_6$haloalkylsulfonyl; and
X is a halogen anion or $BF_4^-$, $PF_6^-$, $HSO_4^-$ or an $C_1$-$C_3$alkylsulfonate, benzenesulfonate or methyl-benzenesulfonate.

2. A process according to claim 1, wherein in the catalyst of formula III
each $R_6$ is vinyl;
each of the substituents $R_7$, $R_8$, $R_9$ and $R_{10}$ has the same meaning and represent halogen and X is chloride or bromide or $BF_4^-$ or $PF_6^-$.

3. A process according to claim 1, wherein in the catalyst of formula III
each $R_6$ is vinyl;
each of the substituents $R_7$, $R_8$, $R_9$ and $R_{10}$ has the same meaning and represent fluoro or chloro; and
X is chloride or bromide.

4. A process according to claim 1, wherein the amount of hydroxylamine is from 1 to 10 equivalents.

5. A process according to claim 1, wherein the amount of base is from 0.05 to 2 equivalents.

6. A process according to claim 1, wherein the amount of catalyst is from 0.01 to 0.4 equivalents.

7. A compound of formula III

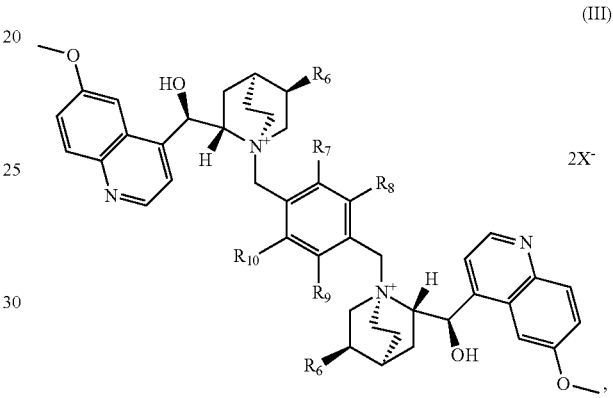

wherein
each $R_6$ is ethyl or vinyl;
$R_7$, $R_8$, $R_9$ and $R_{10}$ are halogen, cyano, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfonyl or $C_1$-$C_6$haloalkylsulfonyl;
and X is a halogen anion, $BF_4^-$, $PF_6^-$ or an $C_1$-$C_3$alkylsulfonate, benzenesulfonate or methyl-benzenesulfonate.

8. A compound of formula III according to claim 7, wherein
each $R_6$ is vinyl;
each of the substituents $R_7$, $R_8$, $R_9$ and $R_{10}$ has the same meaning and represent halogen; and
X is chloride, bromide or $BF_4^-$.

9. A compound of formula III according to claim 7, wherein
each $R_6$ is vinyl;
each of the substituents $R_7$, $R_8$, $R_9$ and $R_{10}$ has the same meaning and represent fluoro or chloro; and
X is chloride or bromide.

* * * * *